US008236254B2

(12) United States Patent
Myles et al.

(10) Patent No.: US 8,236,254 B2
(45) Date of Patent: Aug. 7, 2012

(54) CAP-LINKED TEST STRIP CARRIER FOR VIAL AUGMENTATION

(75) Inventors: Christopher Myles, Alameda, CA (US); Cherie Bulala, Berkeley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 416 days.

(21) Appl. No.: 12/465,942

(22) Filed: May 14, 2009

(65) Prior Publication Data

US 2010/0290956 A1 Nov. 18, 2010

(51) Int. Cl.
*G01N 33/52* (2006.01)

(52) U.S. Cl. ........ 422/401; 206/535; 206/204; 206/540; 206/591; 206/825; 215/228; 215/231; 221/296; 312/294; 312/328

(58) Field of Classification Search .................. 422/401
See application file for complete search history.

(56) References Cited

U.S. PATENT DOCUMENTS 1,488,456 A * 3/1924 Harper .......................... 312/294
4,545,382 A 10/1985 Higgins et al.
4,711,245 A 12/1987 Higgins et al.
5,509,410 A 4/1996 Hill et al.
5,628,890 A 5/1997 Carter et al.
5,723,085 A 3/1998 Abrams et al.
5,820,551 A 10/1998 Hill et al.
5,911,937 A 6/1999 Hekal
6,071,391 A 6/2000 Gotoh et al.
6,120,676 A 9/2000 Heller et al.
6,143,164 A 11/2000 Heller et al.
6,175,752 B1 1/2001 Say et al.
6,299,757 B1 10/2001 Feldman et al.
6,338,790 B1 1/2002 Feldman et al.
6,377,894 B1 4/2002 Deweese et al.
6,461,496 B1 10/2002 Feldman et al.
6,503,381 B1 1/2003 Gotoh et al.
6,514,718 B2 2/2003 Heller et al.
6,540,891 B1 4/2003 Stewart et al.
6,591,125 B1 7/2003 Buse et al.
6,592,745 B1 7/2003 Feldman et al.
6,600,997 B2 7/2003 Deweese et al.
6,618,934 B1 9/2003 Feldman et al.
6,619,819 B2 9/2003 Stowell et al.
6,676,816 B2 1/2004 Mao et al.
6,730,200 B1 5/2004 Stewart et al.
6,736,957 B1 5/2004 Forrow et al.
6,749,740 B2 6/2004 Liamos et al.
6,764,581 B1 7/2004 Forrow et al.
6,773,671 B1 8/2004 Lewis et al.
6,893,545 B2 5/2005 Gotoh et al.
6,942,518 B2 9/2005 Liamos et al.
7,501,093 B2 3/2009 Demelo et al.
7,718,421 B2 * 5/2010 Chen et al. ................. 435/288.5
2003/0185708 A1 10/2003 Otake (Continued)

*Primary Examiner* — Sally Sakelaris
(74) *Attorney, Agent, or Firm* — Edward J. Baba; Michael B. Rubin; Daniel G. Stoddard

(57) ABSTRACT

The present disclosure provides test strip carriers for insertion into test strip vials and methods of making the same. Also provided are test strip vials including test strip carriers, and systems including test strip vials, test strip carriers and analytical test strips. The test strip carriers of the present disclosure are capable of engaging with the caps of test strip vials and thereby facilitating the retrieval of one or more test strips from the test strip vials upon opening of the test strip vials.

28 Claims, 4 Drawing Sheets

U.S. PATENT DOCUMENTS

| | | | | |
|---|---|---|---|---|
| 2004/0007585 | A1 | 1/2004 | Griffith et al. | |
| 2007/0084749 | A1 | 4/2007 | Demelo et al. | |
| 2008/0118400 | A1 | 5/2008 | Neel et al. | |
| 2008/0257905 | A1 * | 10/2008 | Giraud et al. | 221/296 |

* cited by examiner

CAP-LINKED TEST STRIP CARRIER FOR VIAL AUGMENTATION

BACKGROUND

Test strips for analytical purposes are generally supplied to users in test strip vials from which individual test strips are removed as needed. A variety of test strips are known in the art including, for example, those designed to measure the concentration of an analyte in a fluid sample. With currently available test strip vials, it may be difficult for a user to remove a single test strip without tilting and/or shaking the vial, especially when the test strip vial is filled with test strips. Furthermore, tilting and/or shaking of test strip vials may result in undesired test strip spills and potential contamination of test strips. The present disclosure addresses these and related issues in the art.

SUMMARY OF THE INVENTION

The present disclosure provides test strip carriers for insertion into test strip vials and methods of making the same. Also provided are test strip vials including test strip carriers, and systems including test strip vials, test strip carriers and analytical test strips. The test strip carriers of the present disclosure are capable of engaging with the caps of test strip vials and thereby facilitating the retrieval of one or more test strips from the test strip vials upon opening of the test strip vials. These and other objects, features and advantages of the present disclosure will become more fully apparent from the following detailed description of the embodiments, the appended claims and the accompanying drawings.

In a first aspect, the present disclosure provides a test strip carrier for insertion into a test strip vial, wherein the test strip vial includes a cap hingedly coupled to the test strip vial. The test strip carrier includes a first end configured for insertion into the test strip vial and defining a test strip basket, the test strip basket including a base and a wall. The test strip carrier also includes a second end configured to engage the cap and a flexible connector connecting the first end to the second end, wherein the test strip carrier is configured such that when the first end is inserted into the test strip vial and the second end engages the cap, opening of the cap raises the test strip basket from a first position to a second position within the test strip vial.

In one embodiment of the test strip carrier according to the first aspect the wall is an annular wall.

In one embodiment, the second end of the test strip carrier is configured to snapedly engage the cap.

In one embodiment, the second end of the test strip carrier is at least substantially disk shaped.

The test strip carrier according to the first aspect can be formed from a single piece of flexible material. In one embodiment, the flexible material is a polymer. In one embodiment, the flexible material is a polymer, and the polymer is a plastic.

In one embodiment, the second end of the test strip carrier is attached via an adhesive to the cap.

In a second aspect, the present disclosure provides a system including a test strip vial, wherein the test strip vial comprises a cap hingedly coupled to the test strip vial. The system also includes a test strip carrier, wherein the test strip carrier includes a first end configured for insertion into the test strip vial and defining a test strip basket. The test strip basket includes a base and a wall. The test strip carrier also includes a second end configured to engage the cap and a flexible connector connecting the first end to the second end. The system also includes a plurality of test strips disposed in the test strip basket, wherein the test strip carrier is configured such that when the first end is inserted into the test strip vial and the second end engages the cap, opening of the cap raises the test strip basket from a first position to a second position within the test strip vial.

In one embodiment of the system according to the second aspect the wall is an annular wall.

In another embodiment, the second end of the test strip carrier is configured to snapedly engage the cap.

In another embodiment, the second end of the test strip carrier is at least substantially disk shaped.

In the system according to the second aspect, the test strip carrier can be formed from a single piece of flexible material. In one embodiment, the flexible material is a polymer. In one embodiment, the flexible material is a polymer, and the polymer is a plastic.

In a third aspect, the present disclosure provides a test strip vial including a cap hingedly coupled to the test strip vial. The test strip vial also includes a test strip carrier, wherein the test strip carrier includes a first end inserted into the test strip vial, wherein the first end defines a test strip basket. The test strip basket includes a base and a wall. The test strip carrier also includes a second end engaged with the cap and a flexible connector connecting the first end to the second end. Opening of the cap raises the test strip carrier from a first position to a second position within the test strip vial.

In one embodiment of the test strip vial according to the third aspect the wall is an annular wall.

In another embodiment, the second end of the test strip snapedly engages with the cap.

In another embodiment, the second end of the test strip carrier is at least substantially disk shaped.

In the test strip vial according to the third aspect, the test strip carrier can be formed from a single piece of flexible material. In one embodiment, the flexible material is a polymer. In one embodiment, the flexible material is a polymer, and the polymer is a plastic.

In one embodiment, the test strip vial includes a plurality of analytical test strips disposed in the test strip basket.

In one embodiment, the second end of the test strip carrier is attached via an adhesive to the cap of the test strip vial.

In a fourth aspect, the present disclosure provides a method of making a test strip carrier for insertion into a test strip vial having a cap hingedly coupled thereto. The method includes cutting a test strip carrier pattern from a sheet of flexible material and folding the test strip carrier pattern to form a test strip carrier, wherein the test strip carrier includes a first end configured for insertion into the test strip vial and defining a test strip basket. The test strip basket includes a base and a wall. The test strip carrier also includes a second end configured to engage the cap and a flexible connector connecting the first end to the second end. The test strip carrier is configured such that when the first end is inserted into the test strip vial and the second end engages the cap, opening of the cap raises the test strip carrier from a first position to a second position within the test strip vial.

In one embodiment of the method described in the fourth aspect the wall is an annular wall.

In one embodiment, where the wall is an annular wall, the test strip carrier pattern comprises a first engagement slit and a second engagement slit, and the annular wall is formed by engaging the first engagement slit with the second engagement slit.

In one embodiment, the second end of the test strip carrier is configured to snapedly engage the cap of the test strip vial.

In one embodiment, the second end of the test strip carrier is at least substantially disk shaped.

In one embodiment, the flexible material is a polymer. In one embodiment, the flexible material is a polymer, and the polymer is a plastic.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Referring now to the drawings, wherein like reference numerals and letters indicate corresponding structure throughout the several views.

Before the present invention is further described, it is to be understood that this invention is not limited to the particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein and in the appended claims, the singular forms "a," "and," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Test Strip Carriers

Figure 1:
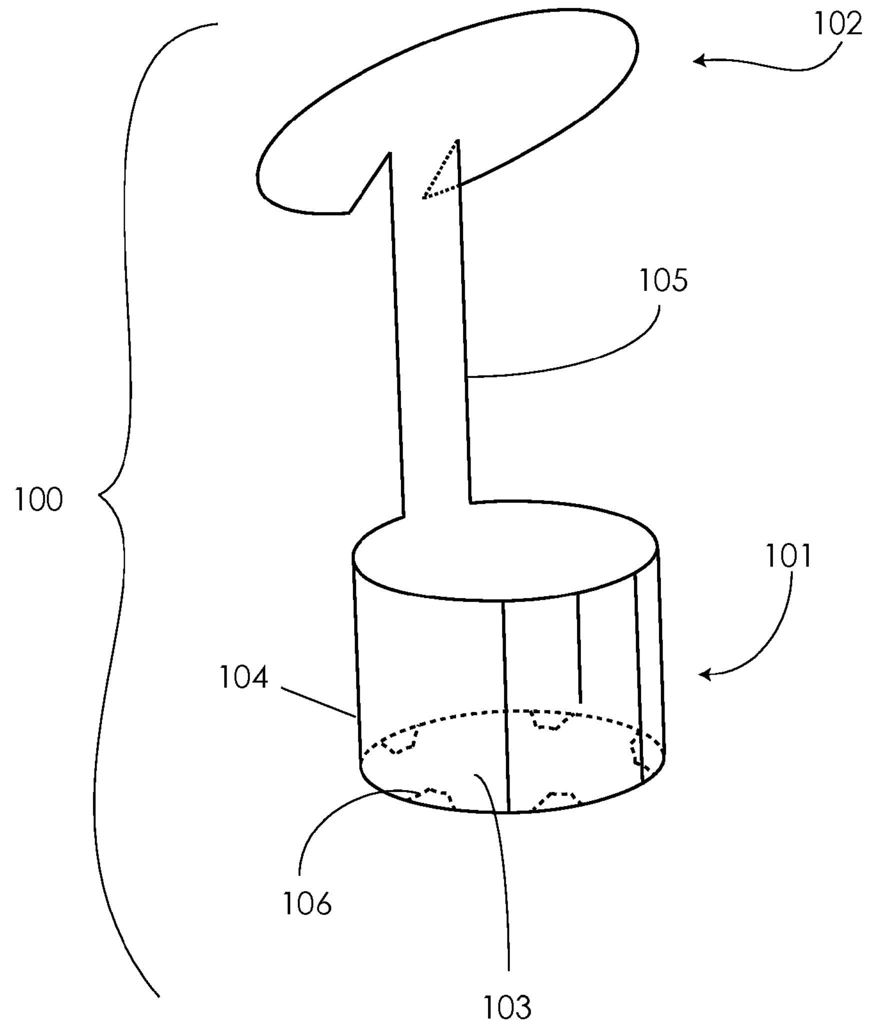
FIG. 1 shows an embodiment of a test strip carrier according to the present disclosure.
Figure 2:
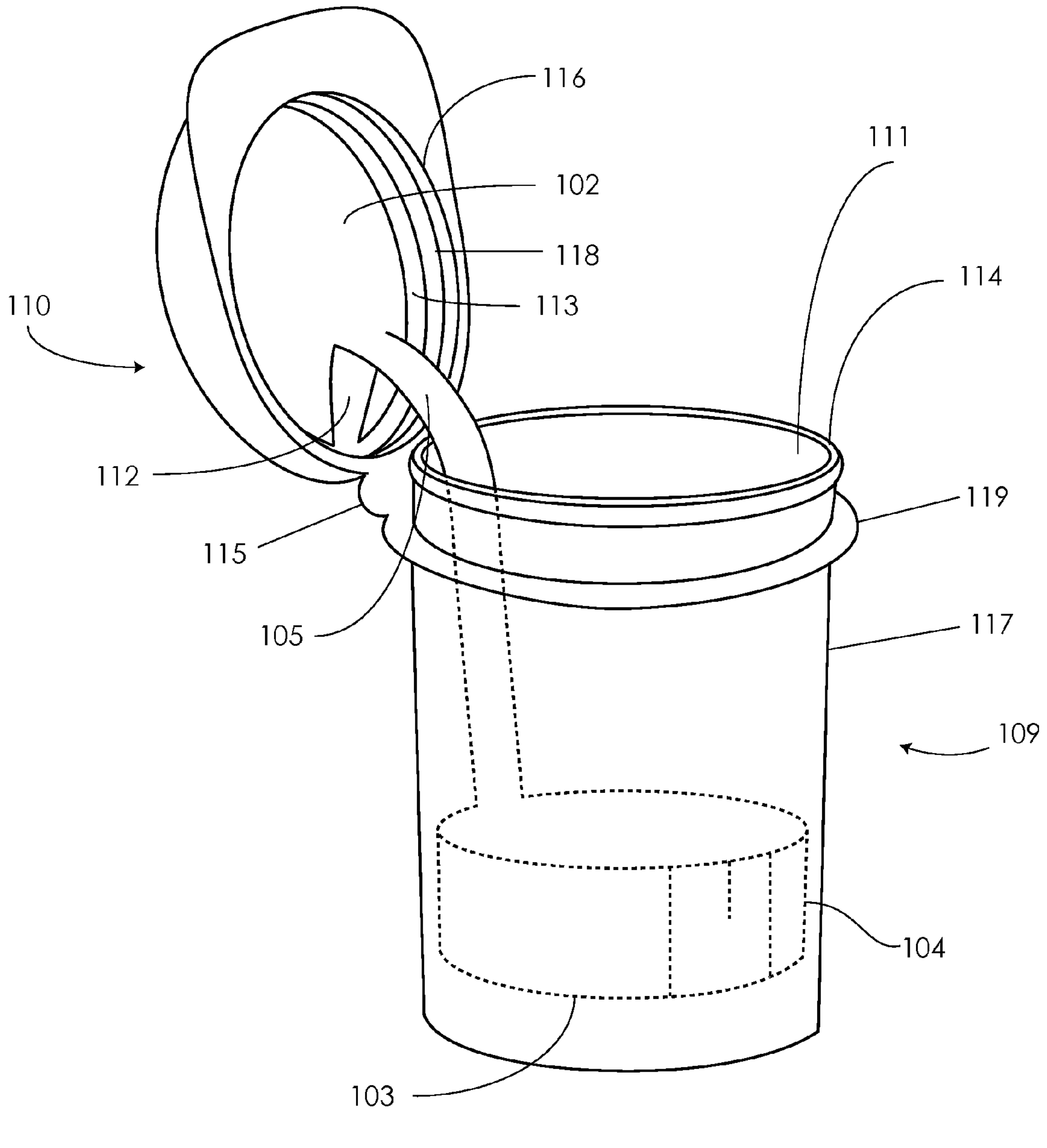
FIG. 2 shows the test strip carrier of FIG. 1 inserted into a test strip vial and engaged with a test strip vial cap.
Figure 3:
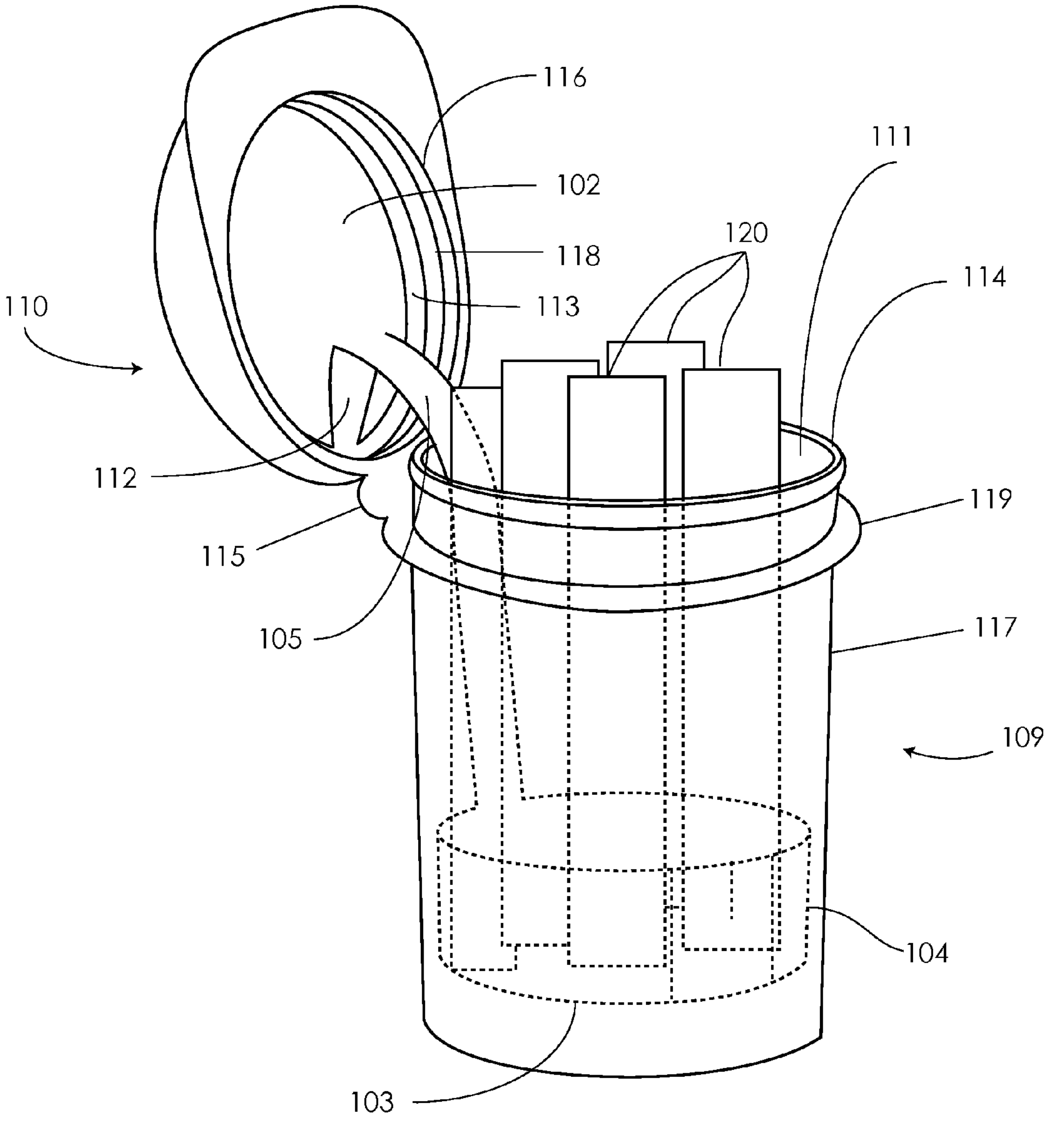
FIG. 3 shows the test strip carrier of FIG. 2 with analytical test strips disposed therein.

As indicated above, the present disclosure provides test strip carriers for insertion into test strip vials. With reference to FIGS. 1, 2 and 3, exemplary embodiments of the test strip carriers of the present disclosure are now described. A test strip carrier 100 includes a first end 101. The first end 101 defines a test strip basket having a base 103 and a wall 104. In the embodiment shown in FIGS. 1, 2 and 3, the wall 104 is an annular wall, although additional configurations are possible, e.g., a wall having one or more 90° angles. As used herein, the term "annular" refers to a shape which is at least substantially circular or elliptical.

With reference to FIG. 1, the test strip carrier 100 optionally includes one or more base tabs 106 which extend from the base of wall 104, and which can be folded during assembly of the test strip carrier such that they engage the base 103 to form the test strip basket. The test strip carrier 100 optionally includes a first engagement slit 107 and a second engagement slit 108 (engagement slits 106 and 107 are visible in the cutout provided in FIG. 4 and are shown in an engaged configuration in FIG. 1). In one embodiment, during formation of the test strip carrier 100, the wall 104 is formed by engaging first engagement slit 107 with second engagement slit 108 or vice versa. The dimensions of the wall 104 may vary. However, the distance from the base 103 to the top of the wall 104 should be less than the length of the test strips 120 held by the test strip basket to facilitate retrieval of the test strips from the test strip basket.

With reference to FIGS. 2 and 3, the first end 101 is configured for insertion into a test strip vial 109 which includes a cap 110 hingedly coupled to the test strip vial 109, e.g., via a hinge or flange. When the test strip carrier 100 is inserted into the test strip vial 109, the first end 101 slidably engages with the inner wall 111 of the test strip vial 109. In other words, first end 101 engages the inner wall 111 via a sliding action. To allow for such slidable engagement, the dimensions of the first end 101 can be configured based on the dimensions of the test strip vial 109 into which the test strip carrier 100 will be inserted. In another embodiment, the test strip vial 109 is configured based on the dimensions of the test strip carrier 100 to be inserted therein.

In one embodiment, the first end 101, is configured such that the outer dimensions of the first end 101, e.g., the circumference of the base including the width of the wall, are sufficiently less than the circumference of the interior wall 111 of test strip vial 109 so as to allow the test strip carrier 100 to slide within the test strip vial 109 with the application of minimal force, e.g., the force applied by a user using one hand to open the test strip vial 109. It may also be desirable to configure test strip carrier 100 such that it engages the inner wall 111 of the test strip vial 109 with sufficient tightness to prevent test strips 120 from sliding past the test strip carrier 100 to the space below the test strip carrier 100 in the test strip vial 109.

In one embodiment, the base 103 optionally includes one or more apertures (not shown) extending through the base 103. These apertures can provide for the exchange of gasses between the area beneath the base 103 and the area above the base 103. Generally, these apertures are sized such that they are large enough to allow for the exchange of gasses between the area beneath the base 103 and the area above the base 103 but small enough to prevent the passage of test strips 120 through the apertures.

The test strip carrier 100 also includes a second end 102, which is configured to engage the cap 110 of the test strip vial 109. Engagement of the cap 110 with the second end 102 may be accomplished in a variety of ways. For example, via application of an adhesive material between the second end 102 and the interior surface 112 of cap 110.

In one embodiment, the second end 102 is configured to detachably engage the cap 110 of the test strip vial 109. In other words, in one embodiment, the test strip carrier is not a component of the cap 110, but is instead a separate component which can detachably engage with the cap 110. Such a configuration is of substantial benefit to the art because the test strip carrier 100 can be readily configured to work with a variety of preexisting test strip vials. In this manner, substantial costs associated with the design and production of new test strip vials and/or retooling of assembly lines can be avoided.

In one embodiment, the second end 102 is configured to snapedly engage, e.g., via a snap feature, the cap 110 of the test strip vial 109. In other words, second end 102 and cap 110 can be configured for snap-fit engagement. For example, in one embodiment second end 102 is at least substantially disk shaped. Where second end 102 is at least substantially disk shaped, it may be sized to snap into annular gap 113 of cap 110.

A flexible connector 105 connects the first end 101 to the second end 102. The flexible connector may take a variety of shapes, provided that the flexible connector is capable of operating as described herein. As shown in FIGS. 1-3, in one embodiment the flexible connector 105 has an elongate rectangular shape.

Overall, the test carrier 100 is configured such that when it is inserted into test strip vial 109, opening of the cap 110 raises the test strip basket from a first position to a second position within the test strip vial 109. For example, with reference to FIG. 3, the pivoting motion of cap 110 about flange 115, moves the cap 110 from a closed position to an open position. Because second end 102 is engaged with the cap 110, the motion of the cap 110 exerts an upward force on the test strip basket via the flexible connector 105. The distance between the first position and the interior surface 112 of cap 110, when the cap 110 is in the closed position, is at least as long as the test strips 120 to be held by the test strip basket. The distance between the second position and the rim 114 of the test strip vial 109 is such that the ends of the test strips 120 will extend beyond the rim 114 of the test strip vial 109 when present. In other words, when a user opens cap 110 of test strip vial 109, the test strip basket is raised within the test strip vial 109 thereby lifting the test strips 120 from a first position closer to the base of the test strip vial 109 to a second position towards the upper edge or rim 114 of test strip vial 109.

Test Strip Vials for Use with the Disclosed Test Strip Carriers

The test strip carriers of the present disclosure can be configured for insertion into a variety of test strip vials known in the art. Vials suitable for use with the test strip carriers disclosed herein are described, for example, in U.S. Pat. Nos. 5,723,085, and 5,911,937, the disclosures of each of which are incorporated by reference herein.

In one embodiment, the test strip carriers of the present disclosure are configured for insertion into a test strip vial 109 as shown in FIGS. 2 and 3. In the embodiment shown in FIGS. 2 and 3, the test strip vial 109 is cylindrical in shape with an integrally formed bottom. The test strip vial 109 includes an interior wall 111. A cap 110 is provided which is adapted to seal the vial closed with a substantially hermetic seal. The cap 110 can be integrally connected to the vial 109 with a small flange 115. In one embodiment, the vial 109 and cap 110 are injection molded from a thermoplastic material.

The cap 110 includes a cap rim 116. The cap rim 116 is intended to fit over the annular rim 114 of the outer wall 117 of the test strip vial 109 in a sealing manner. A ridge 118 may be formed on the inside of cap 110 to enhance the seal of the cap 110 to the vial 109. An annular gap 113 extends from the ridge 118 to the outer edge of interior surface 112 of cap 110.

The test strip vial 109 has an annular ridge 119 extending around the periphery of the test strip vial 109. The annular ridge 119 and a smooth transition surface at the upper edge or rim 114 of the vial 109 form an annular region for interlocking with the cap 110.

The inside of the cap 110, including the ridge 118 and the annular gap 113, combine to form an annular region for interlocking with the interlocking annular region on the vial 109. The inner surface of cap 110 extending from cap rim 116 to ridge 118 is angled so as to guide the upper edge or rim 114 of the vial wall into the annular gap 113. The annular rim 114 of the vial 109 is designed to fit within the annular gap 113.

Analyte Test Strips for Use with the Disclosed Test Strip Carriers

The test strip carriers of the present disclosure can be configured to work with any of a wide variety of analyte test strips. In some embodiments, the test strip carriers of the present disclosure are configured to hold FreeStyle® test strips for use in blood glucose monitoring or Precision® brand test strips for use in monitoring glucose and ketones. FreeStyle® and Precision® brand analyte test strips are available from Abbott Diabetes Care Inc., Alameda, Calif. Exemplary analyte test strips are also described in U.S. Pat. Nos. 6,071,391; 6,120,676; 6,143,164; 6,299,757; 6,338,790; 6,377,894; 6,600,997; 6,773,671; 6,592,745; 5,628,890; 5,820,551; 6,736,957; 4,545,382; 4,711,245; 5,509,410; 6,540,891; 6,730,200; 6,764,581; 6,299,757; 6,338,790; 6,461,496; 6,503,381; 6,591,125; 6,616,819; 6,618,934; 6,676,816; 6,749,740; 6,893,545; 6,942,518; 6,175,752; and 6,514,718, the disclosures of each of which are incorporated by reference herein.

Test strips suitable for use with the test strip carriers described herein include optical and electrochemical test strips configured for use in testing for any of a wide variety of analytes, including, but not limited to, glucose, lactate, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin.

Test strips suitable for use with the test strip carriers described herein also include test strips configured for use in testing for drugs, such as, for example, antibiotics (e.g., gentamicin, vancomycin, and the like), digitoxin, digoxin, drugs of abuse, theophylline, and warfarin, may also be determined and the like.

Materials for Construction

Figure 4:
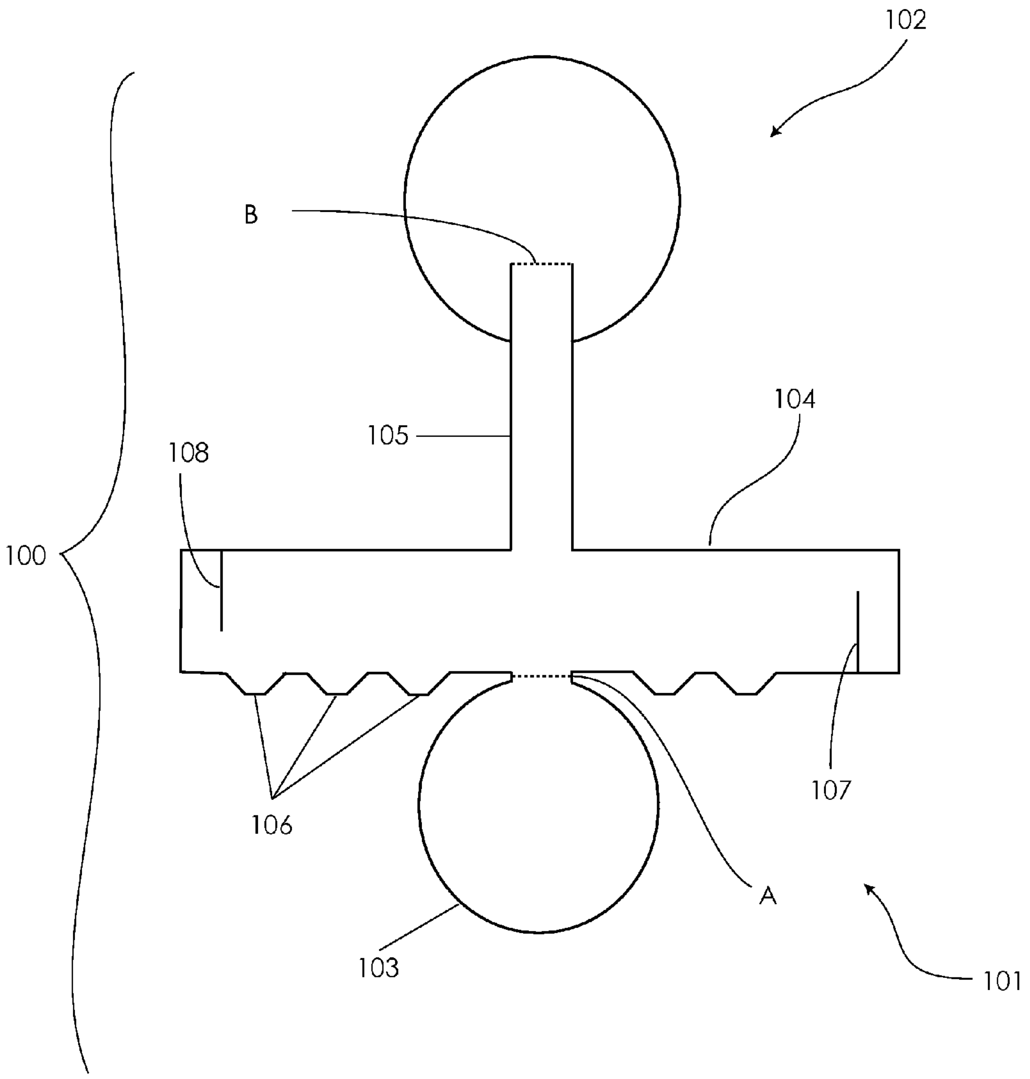
FIG. 4 shows a cutout pattern which can be folded to form a test strip carrier according to the present disclosure.

Test strip carriers according to the present disclosure may be formed and/or constructed from a variety of suitable materials, provided that the materials are sufficiently flexible to operate as described herein. In one embodiment, the test strip carrier is formed from single piece of flexible material, as shown in FIG. 4, which is folded to achieve the final configuration. In another embodiment, the test strip carrier is molded, e.g., injection molded, to achieve the final configuration. Suitable flexible materials include polymers, e.g., plastics. In one embodiment, the flexible material is a thermoplastic polymer, e.g., polycarbonate, polystyrene, polyethylene, polysulfone or polypropylene.

Desiccants

It may be desirable to keep the test strips stored in the test strip vials disclosed herein as moisture free as possible. As such, the test strip vials disclosed herein can include one or more desiccants, e.g., silica gel. The desiccant can be located in the test strip vial or included as a component of the test strip vial itself. The desiccant can also be located on and/or in the material used to form the test strip carrier. In one embodiment the desiccant is included in a moisture absorbing desiccant entrained polymer. This polymer can be used as a component of the test strip vial and/or the test strip carrier. It can also be used to coat one or more surfaces of the test strip vial and/or the test strip carrier. Processes and resulting structures for producing moisture absorbing desiccant entrained polymers are described, for example, in U.S. Pat. No. 5,911,937, the disclosure of which is incorporated by reference herein.

Method of Making

In one embodiment, the test strip carrier 100 is formed from a single piece of flexible material which is folded into the final configuration to be inserted into a test strip vial 109. The single piece of flexible material can be cut from a sheet of flexible material, e.g., a flexible polymer. A variety of methods are known in the art for cutting a predetermined pattern from a sheet of flexible material. Such methods include, but are not limited to, die cutting and laser cutting. These methods can be readily adapted to large scale, high throughput applications as needed.

In one embodiment, the cutout pattern has the configuration shown in FIG. 4. The numeric identifiers in FIG. 4 refer to the structures of the test strip carrier 100 that can be formed from the identified portions of the cutout pattern. The test strip carrier 100 shown in FIGS. 1, 2 and 3 can be formed from the cutout shown in FIG. 4 as follows. The portion of the flexible material forming base 103 is folded at position (A) at an approximately 90° angle relative to the portion of the flexible material which will form the wall 104. The portion of the flexible material which will form the wall 104 is folded such that first engagement slit 107 engages second engagement slit 108 to form wall 104. In another embodiment, the flexible material which will form the wall 104 is folded and engaged with itself via application of an adhesive.

Optional base tabs 106 can be folded at an approximately 90° angle relative to wall 104 such that they engage and/or provide support for base 103. In one embodiment, a plurality of slits (not shown) is provided in base 103. The base tabs 106 can be inserted into these slits in an interlocking manner to provide engagement of the base tabs 106 with the base 103. In another embodiment, the base tabs 106 can engage with base 103 via application of an adhesive. The wall 104 together with base 103 and optional base tabs 108 form the test strip basket in which analytical test strips 120 can be disposed.

Second end 102 is folded at position (B) at one end of flexible connector 105 to form a disk shaped engagement element having a cutout which forms a portion of flexible connector 105 as shown in FIGS. 1, 2 and 3. The fold at position (B) allows the disk shaped engagement element to pivot about the fold axis while engaged with the cap 110 of test strip vial 109.

As indicated above, the test strip carrier can also be molded, e.g., injection molded, to achieve the final configuration.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A test strip carrier for insertion into a test strip vial, wherein the test strip vial comprises a cap hingedly coupled to the test strip vial, the test strip carrier comprising:

a first end configured for insertion into the test strip vial and defining a test strip basket, the test strip basket comprising a base and a wall;

a second end configured to snapedly engage with and fit within the cap; and a flexible connector connecting the first end to the second end, wherein the test strip carrier is configured such that when the first end is inserted into the test strip vial and the second end engages the cap, opening of the cap raises the test strip basket from a first position to a second position within the test strip vial, and wherein the second end stays engaged with the cap upon opening of the cap.

2. The test strip carrier of claim 1, wherein the wall is an annular wall.

3. The test strip carrier of claim 1, wherein the second end is at least substantially disk shaped.

4. The test strip carrier of claim 1, wherein the test strip carrier is formed from a single piece of flexible material.

5. The test strip carrier of claim 4, wherein the flexible material is a polymer.

6. The test strip carrier of claim 5, wherein the polymer is a plastic.

7. The test strip carrier of claim 1, wherein the second end is attached via an adhesive to the cap.

8. A system comprising:

a test strip vial, wherein the test strip vial comprises a cap hingedly coupled to the test strip vial;

a test strip carrier, wherein the test strip carrier comprises a first end configured for insertion into the test strip vial and defining a test strip basket, the test strip basket comprising:

a base and a wall;

a second end configured to snapedly engage with and fit within the cap; and a flexible connector connecting the first end to the second end; and a plurality of test strips disposed in the test strip basket, wherein the test strip carrier is configured such that when the first end is inserted into the test strip vial and the second end engages the cap, opening of the cap raises the test strip basket from a first position to a second position within the test strip vial, and wherein the second end stays engaged with the cap upon opening of the cap.

9. The system of claim 8, wherein the wall is an annular wall.

10. The system of claim 8, wherein the second end is at least substantially disk shaped.

11. The system of claim 8, wherein the test strip carrier is formed from a single piece of flexible material.

12. The system of claim 11 wherein the flexible material is a polymer.

13. The system of claim 12, wherein the polymer is a plastic.

14. A test strip vial comprising:

a cap hingedly coupled to the test strip vial;

a test strip carrier, wherein the test strip carrier comprises a first end inserted into the test strip vial, wherein the first end defines a test strip basket comprising a base and a wall;

a second end snapedly engaged with and fitting within the cap; and a flexible connector connecting the first end to the second end, wherein opening the cap raises the test strip carrier from a first position to a second position within the test strip vial, and wherein the second end stays engaged with the cap upon opening the cap.

15. The test strip vial of claim 14, wherein the wall is an annular wall.

16. The test strip vial of claim 14, wherein the second end is at least substantially disk shaped.

17. The test strip vial of claim 14, wherein the test strip carrier is formed from a single piece of flexible material.

18. The test strip vial of claim 17 wherein the flexible material is a polymer.

19. The test strip vial of claim 18, wherein the polymer is a plastic.

20. The test strip vial of claim 14, wherein the test strip vial comprises a plurality of analytical test strips disposed in the test strip basket.

21. The test strip vial of claim 14, wherein the second end is attached via an adhesive to the cap.

22. A method of making a test strip carrier for insertion into a test strip vial having a cap hingedly coupled thereto, the method comprising:

cutting a test strip carrier pattern from a sheet of flexible material;

folding the test strip carrier pattern to form a test strip carrier, the test strip carrier comprising:

a first end configured for insertion into the test strip vial and defining a test strip basket, the test strip basket comprising a base and a wall;

a second end snapedly engaged with and fitting within the cap; and a flexible connector connecting the first end to the second end, wherein the test strip carrier is configured such that when the first end is inserted into the test strip vial and the second end engages the cap, opening of the cap raises the test strip carrier from a first position to a second position within the test strip vial, and wherein the second end stays engaged with the cap upon opening of the cap.

23. The method of claim 22, wherein the wall is an annular wall.

24. The method of claim 22, wherein the test strip carrier pattern comprises a first engagement slit and a second engagement slit, and wherein the annular wall is formed by engaging the first engagement slit with the second engagement slit.

25. The method of claim 22, wherein the second end is configured to snapedly engage the cap.

26. The method of claim 22, wherein the second end is at least substantially disk shaped.

27. The method of claim 22, wherein the flexible material is a polymer.

28. The method of claim 27, wherein the polymer is a plastic.

* * * * *